(12) United States Patent
Bonechi et al.

(10) Patent No.: US 6,516,083 B1
(45) Date of Patent: Feb. 4, 2003

(54) ELECTRO-OPTICAL UNIT FOR SCANNING THE ENTIRE LATERAL SURFACE OF ARTICLES SUBSTANTIALLY CYLINDRICAL IN SHAPE

(75) Inventors: Alberto Bonechi, Bologna (IT); Luca Cerati, Bologna (IT); Armando Neri, Bologna (IT)

(73) Assignee: G. D S.p.A., Bologna (IT)

( * ) Notice: Subject to any disclaimer, the term of this patent is extended or adjusted under 35 U.S.C. 154(b) by 0 days.

(21) Appl. No.: 09/252,994

(22) Filed: Feb. 19, 1999

(30) Foreign Application Priority Data

Feb. 23, 1998 (IT) ......................................... BO98A0103

(51) Int. Cl.[7] ............................. G06K 9/00; A24C 5/34; H01J 40/14; G01N 21/00
(52) U.S. Cl. ........................ 382/141; 131/280; 250/223; 356/237.1
(58) Field of Search ................................ 382/312, 141, 382/143; 250/223 R; 209/524; 356/237.1, 237.2, 421, 430; 131/280

(56) References Cited

U.S. PATENT DOCUMENTS

| | | | |
|---|---|---|---|
| 3,728,145 A | * 4/1973 | Hjerten | ........................ 204/600 |
| 4,377,743 A | * 3/1983 | Bolt et al. | ............... 250/223 R |
| 5,118,193 A | 6/1992 | Brown | ........................ 356/394 |
| 5,781,306 A | * 7/1998 | Hartig et al. | ................. 356/436 |
| 5,936,725 A | * 8/1999 | Pike et al. | ................. 356/237.1 |
| 5,990,503 A | * 11/1999 | Ingram et al. | ............... 257/236 |

FOREIGN PATENT DOCUMENTS

| | | | |
|---|---|---|---|
| EP | 570 163 A2 | 11/1993 | .......... G01N/21/88 |
| EP | 582 868 A1 | 2/1994 | .......... G01N/21/88 |
| EP | 639 764 A1 | 2/1995 | .......... G01N/21/88 |

OTHER PUBLICATIONS

Patent Abstracts of Japan, vol. 013, No. 351 (P–912), Aug. 7, 1989 & JP 01 112143 A, Apr. 28, 1989.
Patent Abstracts of Japan, vol. 010, No. 271 (P–497), Sep. 16, 1986 & JP 61 093935 A, May 12, 1986.

* cited by examiner

*Primary Examiner*—Wenpeng Chen
(74) *Attorney, Agent, or Firm*—The Law Offices of Timothy J. Klima

(57) ABSTRACT

A continuous cigarette rod advancing along a set path is directed through an electro-optical scanning station where its entire cylindrical surface is inspected by a unit comprising an illumination device of which the function is to shed light in substantially uniform manner on a given annular area of the surface, a line scan television camera positioned relative to the path in such a way as to enable acquisition of a direct image from a first portion of the annular area, and a reflecting element located on the side of the path opposite to the camera, embodied and oriented in such a way as to reflect two images back toward the camera which combine with the direct image to make up the entire annular area.

11 Claims, 1 Drawing Sheet

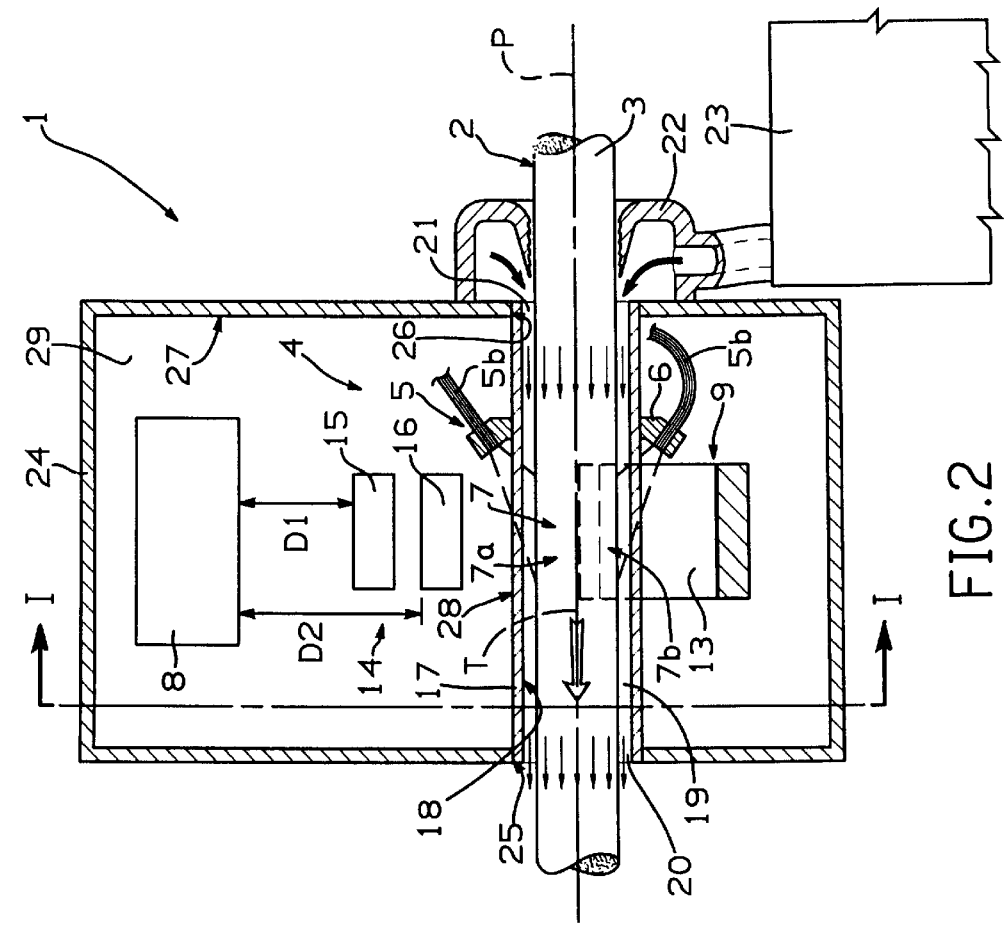
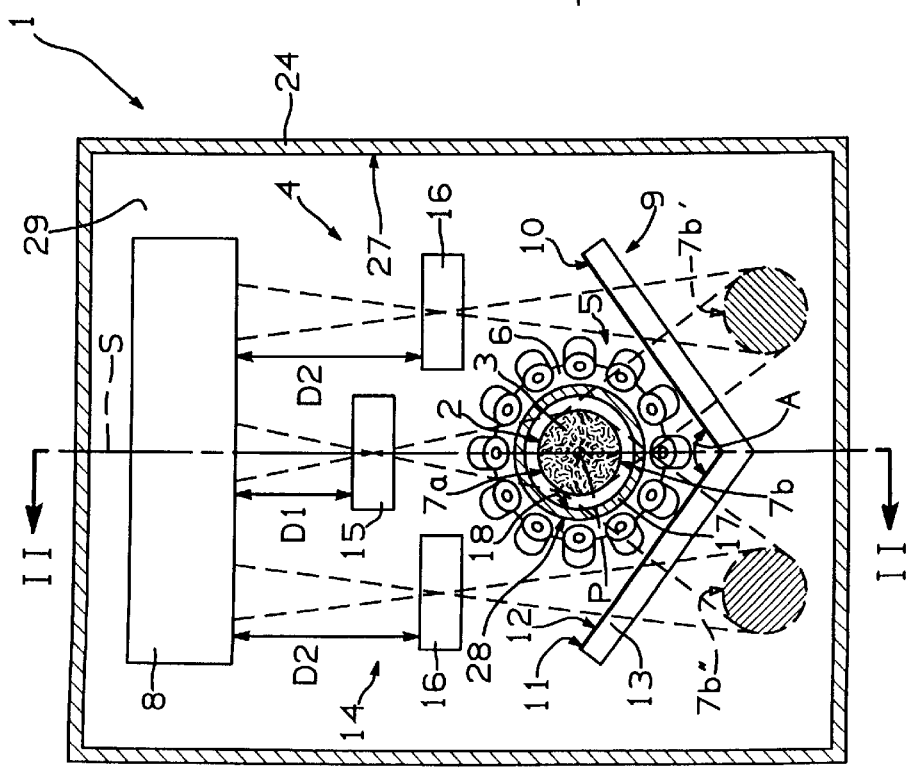
FIG. 1
FIG. 2

ELECTRO-OPTICAL UNIT FOR SCANNING THE ENTIRE LATERAL SURFACE OF ARTICLES SUBSTANTIALLY CYLINDRICAL IN SHAPE

BACKGROUND OF THE INVENTION

The present invention relates to an electro-optical unit for scanning the entire lateral surface of articles appearing substantially cylindrical in shape.

The invention finds application to advantage in the tobacco industry, an art field to which direct reference is made in the following specification albeit with no limitation in general scope implied.

In particular the unit according to the invention can be used in cigarette or filter manufacturing machines to inspect the entire lateral cylindrical surface of continuous cigarette or filter rods, or of the discrete lengths cut from such rods.

Referring particularly to cigarette manufacturing machines, it is conventional practice to employ a substantially vertical duct having a bottom infeed end supplied with an ascending and continuous flow of tobacco particles, and a top outlet end directed at an aspirating belt on which a continuous fillet of tobacco filler is formed.

The tobacco filler is deposited by the aspirating belt on a continuous strip of cigarette paper with gummed longitudinal edges supported by a looped conveyor belt, whereupon the paper is forced by this same belt to wrap around the filler, the two gummed edges are brought into overlapping contact and a continuous cigarette rod of substantially cylindrical shape is formed.

The continuous cigarette rod is caused to advance along a substantially rectilinear and horizontal path toward a cutter device with a rotating blade by which it is divided into discrete portions of predetermined and constantly repeated length.

The paper surface of a cigarette rod fashioned in the manner described above may exhibit a variety of flaws, for example: a defective overlapping join between the longitudinal edges of the paper strip, laceration of the paper caused by impurities in the tobacco filler, stains, deformations, etc.

In order to detect such imperfections and others, the prior art embraces the use of electro-optical scanning units; these units typically comprise a support element in the form of a ring through which the cigarette rod is directed, centrally aligned, a first set of optical fiber light guides connected at one end to a single light source, of which the respective opposite ends are distributed uniformly along a peripheral internal surface of the ring in such a manner as to illuminate an annular area of the cylindrical surface presented by the cigarette rod, and a second set of optical fiber light guides with one set of ends distributed uniformly around the peripheral internal surface of the ring in such a way as to pick up the light reflected by the rod, and the opposite ends connected to a sensing device equipped with photosensitive elements, typically photodiodes or phototransistors.

The photosensitive elements of the sensing device are connected electrically to a comparator that will generate an error signal whenever at least one of the photosensitive elements returns an output signal of value different to a selected reference signal.

It happens with units of this type, when defects in the lateral surface of the continuous cigarette rod are detected, that variations in amplitude of the resulting output signals can become confused with certain variations in the background noise that is generated typically by the photosensitive elements in response to vibrations transmitted inevitably by the advancing cigarette rod.

To avoid the eventuality of the comparator giving false error signals, background noise components are generally filtered out by special electronic processing circuits. Nonetheless, the imperfections it is wished to detect are often missed when using such circuits, which also have the disadvantage of being relatively complex.

In addition, there is the drawback that units of the type in question are themselves somewhat costly in overall terms.

The object of the present invention is to provide an electro-optical unit for scanning the entire lateral surface of articles appearing substantially cylindrical in shape, such as will be more simple, more economical and more reliable than those of the conventional type described above.

SUMMARY OF THE INVENTION

The stated object is realized according to the invention in an electro-optical unit for scanning the entire lateral surface presented by articles of substantially cylindrical shape advancing along a predetermined path, comprising illumination means located at a scanning station positioned along the selfsame path, of which the function is to shed light on a given annular area of the surface in substantially uniform manner, and, located at the scanning station, television camera type image detection means of which the position relative to the path is such as to allow the acquisition of a direct image from a first portion of the annular area, and reflecting means located on the side of the path opposite to the detection means, embodied and oriented in such a way that at least one image from a second portion of the annular area can be reflected back toward the detection means.

BRIEF DESCRIPTION OF THE DRAWINGS

The invention will now be described in detail, by way of example, with reference to the accompanying drawings, in which:

FIG. 1 illustrates a possible embodiment of the electro-optical scanning unit according to the invention, viewed in a front elevation with certain parts in section and others omitted for clarity;

FIG. 2 is a sectional view of the unit taken on II—II in FIG. 1.

DESCRIPTION OF THE PREFERRED EMBODIMENTS

In the two drawings, 1 denotes an electro-optical scanning unit, in its entirety, designed to inspect the whole of the substantially cylindrical lateral surface 2 of a continuous cigarette rod 3 caused to advance longitudinally (by conventional means not illustrated in the drawings) along a substantially rectilinear and horizontal path P.

The unit 1 is installed at a scanning station 4 located along the path P, occupying a substantially symmetrical position relative to a vertical plane S with which the path P coincides.

The unit comprises an illumination device 5 which in turn comprises a light source (not illustrated) and a plurality of optical fiber light guides 5b (see FIG. 2) having one set of ends grouped together and located near to the light source (not shown), and the opposite set of ends distributed uniformly around the outer periphery of an annular support element 6 coaxial with the path P. In particular, the ends distributed around the annular element 6 are oriented relative to the path P in such a way as to shed light on a selected annular area 7 of the surface 2 in substantially uniform manner.

The unit 1 also comprises a TV camera 8 disposed facing the path P and positioned in such a way as to frame a given portion 7a of the area 7 extending symmetrically in relation to the vertical plane S through an arc compassing substantially 180°. In a preferred embodiment of the unit, the camera 8 will be a CCD array Line Scan, or alternatively a CCD array Time Delay and Integration Line Scan type.

The unit 1 further comprises a reflecting optical element denoted 9, positioned on the side of the path P opposite from the camera 8 and consisting in two flat reflecting surfaces 10 and 11 disposed symmetrically in relation to the vertical plane S and directed toward the cigarette rod 3, forming a predetermined angle A and combining to create the reflecting face 12 of a single thin wall 13 of Vee shape. The angle A is selected in such a way that with the unit in operation, the surfaces 10 and 11 will reflect two respective images back toward the camera 8 which are relative to two portions 7b' and 7b" of the annular area 7 extending through an arc substantially of 180° and representing a portion 7b that combines with the portion 7a already mentioned to make up the annular area 7 in its entirety.

14 denotes a focusing device associated with the camera 8, which comprises a single focusing lens 15 disposed facing the path P at a given distance D1 from the camera 8, and a pair of focusing lenses 16 disposed symmetrically on opposite sides of the vertical plane S, facing the respective reflecting surfaces 10 and 11, likewise at a given distance D2 from the camera 8. The distances D1 and D2 are such that the images of the respective portions 7a and 7b'–7b" will be focused onto a single plane.

Also forming part of the unit is a substantially cylindrical transparent tubular element denoted 17, embodied in quartz and extending coaxially along a given stretch T of the path P, of which the bore is greater than the diameter of the cigarette rod 3, and by which the cigarette rod 3 is shielded from the illumination device 5, the TV camera 8, the reflecting element 9 and the focusing device 14; the function of the cylindrical tubular element 17 is to protect these components from foreign matter (grit, dust, tobacco particles, etc.) carried along by the cigarette rod 3 as it advances toward the scanning station 4.

The internal surface 18 of the transparent tubular element 17 combines with the lateral surface 2 of the cigarette rod 3 to establish a chamber 19 of which one end 20 is open and the opposite end 21 is connected in substantially fluid tight association to an annular manifold 22, connected in its turn to an air compressor 23.

Lastly, the unit 1 comprises a housing 24 such as will accommodate the illumination device 5, the TV camera 8, the reflecting device 9, the focusing device 14 and the tubular element 17, and which affords two substantially circular openings 25 and 26 interconnected by the tubular element 17. More exactly, an internal surface 27 of the housing 24 combines with an external surface 28 of the tubular element 17 to create a substantially fluid tight chamber 29 containing the illumination device 5, the TV camera 8, the reflecting device 9 and the focusing device 14.

In operation, the continuous cigarette rod 3 is advanced longitudinally (by conventional means not illustrated in the drawings) along the path P and through the scanning station 4.

More exactly, the rod 3 is directed along the entire stretch T of the path P, passing internally of the tubular element 17 and therefore through the housing 24, inside which the illumination device 5 sheds its light through the tubular element 17 and onto the annular area 7 of the lateral surface 2 presented by the rod 3.

The camera 8 picks up a direct image of the one portion 7a through the one lens 15, whereas the remaining portion 7b is a composition of the two images reflected through the pair of lenses 16 by the surfaces 10 and 11 offered to the two portions denoted 7b' and 7b". In this way an inspection is made of the entire annular area 7, and consequently of the entire lateral surface 2, as the cigarette rod 3 passes through the scanning station 4.

The complete inspection of the surface 2 effected in the manner described above means not only that flaws will be detected, but also that the diameter of the cigarette rod can be monitored continuously, and any deviation of the diametral value from a preset reference readily identified.

The provision of a chamber 29 guarantees that the illumination device 5, the camera 8, the reflecting surfaces 10 and 11 of the reflecting element 9 and the lenses 15 and 16 of the focusing device 14 will be kept clean, while air blown continually through the tubular element 17 by the compressor 23 during the movement of the rod 3 ensures that the inside surface 18 of the element 17 also stays clean.

The unit 1 could be embodied equally well without any focusing device, the camera 8 in this instance being positioned at a distance from the cigarette rod 3 and from the reflecting element 9 such that the direct and reflected images of the respective portions 7a and 7b'–7b" will be substantially in focus.

Whilst the reflecting element illustrated in the drawings is embodied with two reflecting surfaces, it would also be possible to use more than two such surfaces, and without prejudice to the scope of the protection afforded by the appended claims.

Finally, it will be seen that the quality control methods described above obviously could be utilized to good effect for inspecting the entire lateral cylindrical surface of discrete cigarettes cut from a continuous rod 3, likewise of discrete filters, and caused to advance perhaps transversely to their longitudinal axis.

What is claimed is:

1. An electro-optical unit for scanning the entire lateral surface presented by articles of substantially cylindrical shape advancing along a predetermined path, comprising illumination means located at a scanning station positioned along the selfsame path, of which the function is to shed light on a given annular area of the surface in uniform manner, and, located at the scanning station, television camera type image detection means of which the position relative to the path is such as to allow the acquisition of a direct image from a first portion of the annular area, also reflecting means located on the side of the path opposite to the detection means, embodied and oriented in such a manner that at least one image from a second portion of the annular area can be reflected back toward the detection means, a tubular element of transparent material coinciding at least with the scanning station, through which the articles are caused to pass, wherein the illumination means, the detection means and the reflecting means are disposed externally of the tubular element, and a housing element of which an internal surface encloses the illumination means, the detection means and the reflecting means, and of which the internal space is occupied by the tubular element, wherein an external surface of the tubular element combines with the internal surface of the housing element to create a fluid-tight chamber containing the illumination means, the detection means and the reflecting means.

2. A unit as in claim 1, wherein reflecting means comprise two flat reflecting surfaces disposed at a selected angle one relative to another, positioned in such a way that the detection means will receive two respective reflected images combining with the direct image to represent the entire annular area.

3. A unit as in claim 2, wherein reflecting means comprise a wall with a Vee shaped reflecting face of which the two reflecting surfaces constitute two respective parts.

4. A unit as in claim 1, wherein the image detection means are charge coupled device array line scan type means.

5. A unit as in claim 1, wherein the image detection means are charge coupled device array time delay and integration line scan type means.

6. A unit as in claim 1, wherein the tubular element is substantially cylindrical and disposed coaxially with the path.

7. A unit as in claim 1, wherein the tubular element is fashioned from quartz.

8. A unit as in claim 1, comprising pneumatic means by which the internal surface of the tubular element is kept clean.

9. A unit as in claim 1, comprising optical focusing means by which the images of the first portion and of the second portion of the annular area are focused onto a single plane.

10. A unit as in claim 1, comprising optical focusing means by which the images of the first portion and of the second portion of the annular area are focused onto a single plane, wherein such optical focusing means are disposed externally of the tubular element.

11. A unit as in claim 1, wherein the chamber contains the optical focusing means.

* * * * *